United States Patent [19]

Richter et al.

[11] Patent Number: 4,976,258
[45] Date of Patent: Dec. 11, 1990

[54] LOCKING NAIL

[75] Inventors: Karl M. Richter, Wendtorf, Fed. Rep. of Germany; Vilmos Vecsei, Vienna, Austria

[73] Assignee: Howmedica International, Inc., Kiel, Fed. Rep. of Germany

[21] Appl. No.: 191,745

[22] Filed: May 5, 1988

Related U.S. Application Data

[63] Continuation of Ser. No. 14,567, Feb. 13, 1987, abandoned, which is a continuation of Ser. No. 585,313, Mar. 1, 1984, abandoned.

[30] Foreign Application Priority Data

Sep. 9, 1983 [DE] Fed. Rep. of Germany ....... 8306675

[51] Int. Cl.$^5$ ................................................ A61F 5/04
[52] U.S. Cl. ..................................................... 606/64
[58] Field of Search ........... 128/92 B, 92 BC, 92 BA, 128/92 BB, 92 R, 92 Y, 92 YZ, 92 YK, 92 YS, 92 YE

[56] References Cited

U.S. PATENT DOCUMENTS

| | | | |
|---|---|---|---|
| Re. 28,502 | 8/1975 | Burstein et al. | 128/92 BC |
| 2,136,471 | 11/1938 | Schneider | 128/92 BC |
| 2,675,801 | 4/1954 | Bambara et al. | 128/92 BC |
| 3,893,196 | 7/1975 | Hochman | 128/92 BC |
| 3,977,398 | 8/1976 | Burstein | 128/92 BC |
| 4,040,129 | 8/1977 | Steinmann et al. | 3/1.9 |
| 4,103,683 | 8/1978 | Neufeld | 128/92 BA |
| 4,375,810 | 3/1983 | Belykh et al. | 128/92 R |
| 4,446,857 | 5/1984 | Otte et al. | 128/92 BC |
| 4,475,545 | 10/1984 | Ender | 128/92 G |
| 4,541,424 | 9/1985 | Grosse et al. | 128/92 EB |
| 4,550,723 | 11/1985 | Belykh et al. | 128/92 B |

FOREIGN PATENT DOCUMENTS

| | | | |
|---|---|---|---|
| 2288506 | 5/1976 | France | 128/92 BC |
| 1593440 | 7/1981 | United Kingdom . | |

*Primary Examiner*—Gene Mancene
*Assistant Examiner*—J. Hakomaki
*Attorney, Agent, or Firm*—Charles J. Knuth; Peter C. Richardson; Lawrence C. Akers

[57] ABSTRACT

A hollow elongated medullary bone nail capable of being locked in place with at least a pair of transversely-disposed bone screws is disclosed. The radius in transverse cross-section of the outer surface of the nail varies over the circumference of the cross-sectional profile of the nail in such a manner that a steadily rounded contour results.

6 Claims, 1 Drawing Sheet

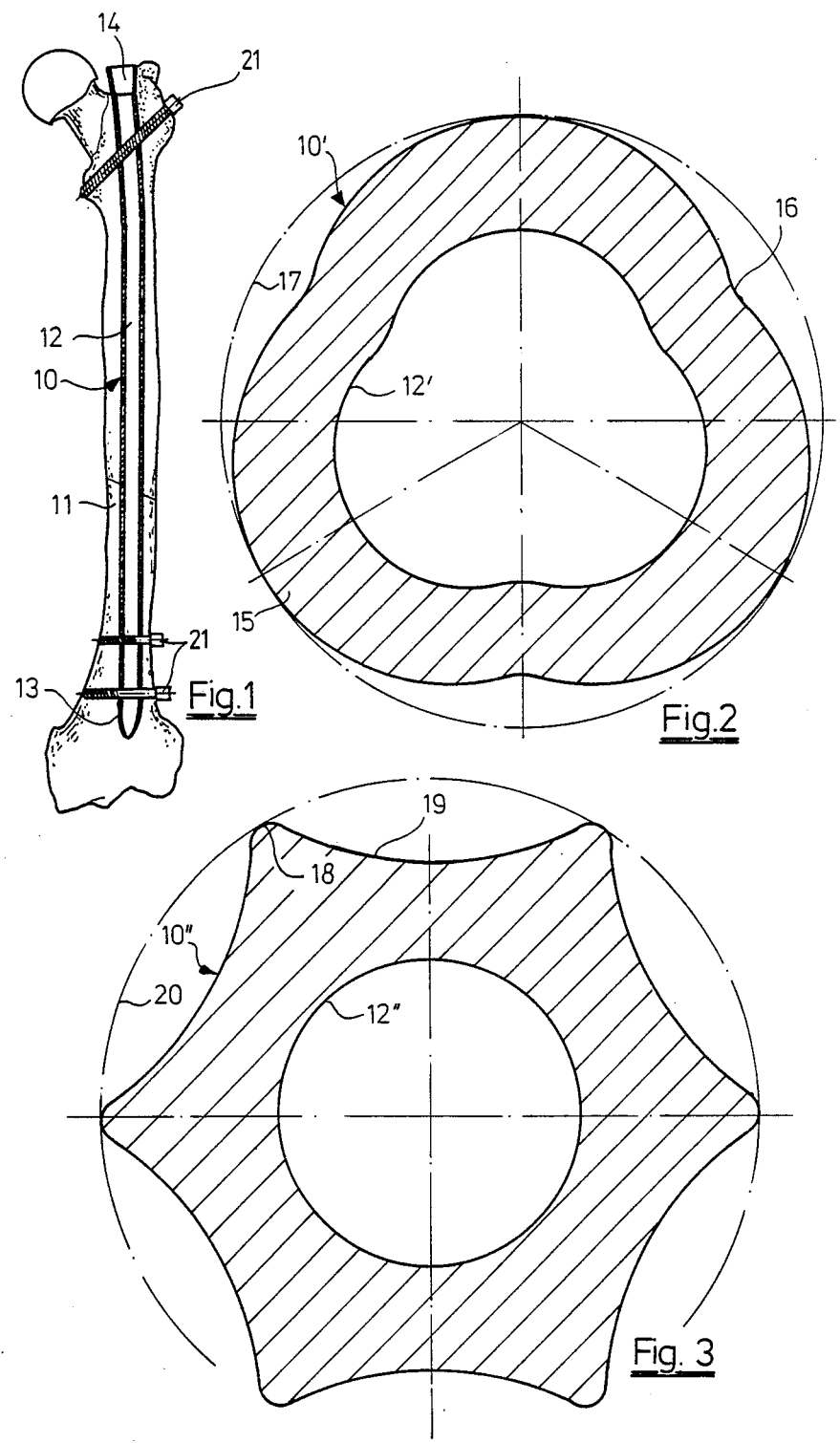

LOCKING NAIL

This is a continuation of application Ser. No. 014,567, filed on Feb. 13, 1987, abandoned, which in turn is a continuation of application Ser. No. 585,313, filed Mar. 1, 1984, and now abandoned.

BACKGROUND OF THE INVENTION

The invention relates to a locking nail for the treatment of bone fractures, comprising an elongated hollow member which is tapered at the front end while having an enlargement at the end by which it is driven in for the accommodation of a driving tool, said member being provided with at least one pair of transverse bores for the accommodation of a bone screw.

Locking nails are medullary nails which are driven into the medullary canal. The position of transverse bores in the locking nail is detected via image commutators, so that transverse bores are formed in the bone in conformity with the above transverse bores and via which bone screws may then be screwed into the bone and the locking nail. In this manner, the locking nail may be fastly connected to the bone on both sides of the fracture. Locking nails serve in particular for the treatment of smashed fractures which cannot be sufficiently treated with the usual medullary nails (Küntscher nails). This above all, because smashed fractures render a bone extremely instable as to rotation, and stability of rotation cannot be obtained by means of a normal medullary nail.

The known locking nails are modeled after the known Küntscher nails, i.e. they have a so-called clover-leaf profile in cross section. They furthermore have a longitudinal slot extending the greater part of the length of the nail body, with only the ends of the nail forming a closed profile. It has been found, however, that a slotted nail permits of a certain torsion and, above all, has relatively sharp edges, which may lead to injuries and thus may bring about a danger of perforation for the bone.

SUMMARY OF THE INVENTION

It is therefore the object of the innovation to provide a bone nail, especially a locking nail, which is distinguished for a high degree of rotational stability and which does not affect the bone.

In accordance with the innovation this object is attained in that the cross sectional profile is closed in the shape of a ring over the circumference thereof and the radius of the outer surface changes over the circumference in such a manner that a steadily rounded contour results.

The annular closed cross sectional profile of the nail in accordance with the innovation has a high moment of resistance and thus brings about a high rotational stability. The outer contour of the nail deviating from the circular shape makes possible a more or less marked engagement in the medullary canal, in order to avoid a relative rotation between the bone and the nail. But simultaneously, the rotational engagement is such that injury or even perforation of the bone is precluded, i.e. by rounded transitions. It might be imagined, indeed, to provide the outer contour with more or less sharp blade-like edges, in order to obtain a particularly marked rotational engagement. Such an outer contour, however, as already stated above, may possibly lead to injury of the bone.

According to one embodiment of the innovation provision is made for the cross sectional profile to comprise alternate elevations and deepenings over the circumference. As already mentioned, the transitions between the elevations and deepenings must be steady and possibly smooth, so as to reduce the danger of injuries.

In one embodiment of the innovation provision is made in this connection for the radially farthest outwardly and radially farthest inwardly disposed points of the elevations and deepenings to lie on a circular path concentric with respect to the axis. Such an embodiment may be realised, for example, in accordance with another embodiment of the innovation by three circular elevations uniformly spaced circumferentially with relatively flat rounded deepenings interposed between them.

As an alternative to the above, in accordance with another embodiment of the innovation, the cross sectional profile may be in the shape of a Maltese cross with rounded tooth peaks.

Such nails which may have a diameter from 9 to 18 mm are often driven in with the aid of a so-called guiding spear having been driven into the bone before. For this purpose the nail must be provided with a continuous longitudinally extending canal for the guiding spear. According to one embodiment of the innovation the inner canal is circular in cross section. It has, however, a configuration deviating from the circular shape when the wall is approximatley uniformly thick in cross section over the circumference. In this case, the inner wall of the canal follows the outer contour of the nail.

The material of the nail according to the innovation, naturally, consists of system compatible non-corroding material. It is at the same time suited to be produced in an extrusion process. The extrusion process prevents the information of seams and burrs at the periphery of the nail, which are extremely undesired.

DETAILED DESCRIPTION OF THE INVENTION

Examples of embodiment of the innovation will be shown in the following in more detail by way of drawings.

FIG. 1 shows a sectional view of a locking nail implanted in a femur.

FIG. 2 shows a sectional view of a locking nail according to the innovation.

FIG. 3 shows a sectional view of a locking nail according to another embodiment of the innovation.

Prior to enlarging in more detail on the individual representations in the drawings, it has to be stated that each of the features shown and described is of essential importance to the innovation by itself or in connection with features of the claims.

In FIG. 1 a locking nail 10 is driven into a femur 11 from the trochanter major. The locking nail 10 comprises a hollow profile with a through-going inner canal 12 extending as far as the tapered peak 13 of the nail 10. In this manner with a guiding spear being used the nail 10 may be driven in along the guiding spear (as is generally known in connection with the nailing according to Küntscher). At the end of the beating-in the nail 10 is provided with a conical enlargement 14 formed with an inner thread which may be brought into engagement with a tool.

It is a requirement to be met in the method of nailing that the position of pairs of transverse bores is detected with the aid of an image commutator after the locking nail 10 has been driven in, in order to bore a hole into the corticalis in the common axis of a pair of bores for the purpose of threading in transverse screws 21. In the representation according to FIG. 1 transverse bone screws 21 are respectively threaded in on either side of the smashed fracture. The uppermost in this arrangement is inserted obliquely, in correspondence with the transbores provided therefor in the nail 10.

The nail 10 may have a cross sectional profile as shown in FIG. 2. The nail 10' has a cross section in the shape of a "clover leaf profile" with three elevations 15 circumferentially spaced through 120° the outer contour of which is circularly shaped with the circular arcs subtending an angle of about 90°. Interposed between the elevations 15 are deepenings 16 or grooves with the elevations 15 passing over into the deepenings 16 through a rounded smooth transition as shown in FIG. 2.

The wall of the nail 10 is of uniform thickness all over the entire circumference, so that the canal 12' has an inner contour corresponding to the outer contour of the nail 10'. The elevations have the highest points thereof disposed on a common circular arc 17. This applies correspondingly also to the deepenings 16. The locking nail shown has a high moment of resistance with relatively little expenditure in terms of material.

FIG. 3 shows the cross sectional area of a locking nail 10" the outer contour of which resembles a Maltese cross having six uniformly circumferentially spaced tooth peaks 18 rounded in the shape of a circular arc. A corresponding flute 19 is provided between the tooth peaks, which passes over into the peaks 18 through a soft transition. The tooth peaks 18 are disposed on a circular arc 20 concentric with respect to the axis of the nail 10". The inner canal 12" is circularly shaped in cross section.

I claim:

1. A bone nail for the treatment of bone fractures comprising an elongated hollow body tapered at the front end and having an enlargement at the rear end by which it is driven into a bone of a patient for the accommodation of a driving tool and at least one pair of transverse bores for the accommodation of bone screws, one of said bores being adjacent the front end of said body and one of said bores being adjacent the rear end of said body, with the cross-sectional profile of said body being closed over the circumference of said profile in the shape of a ring, and with the radius of the outer surface of said body changing over said circumference in such a manner that a steadily rounded contour results and said outer surface is provided with alternating elevations and depressions over the circumference thereof.

2. A bone nail according to claim 1 wherein the points of the elevations and depressions disposed farthest radially outward and farthest radially inward are each disposed on a circular arc concentric with respect to the axis of the nail.

3. A bone nail according to claim 2 wherein said cross-sectional profile is provided with three circular-shaped elevations uniformly spaced over the circumference thereof with relatively flatly rounded depressions disposed therebetween.

4. A bone nail according to claim 2 wherein said cross-sectional profile corresponds to a Maltese cross with rounded tooth peaks.

5. A bone nail according to claim 1 wherein the inner canal of said elongated hollow body is circularly-shaped in cross-section.

6. A bone nail according to claim 2 wherein the wall of said elongated hollow body is of approximately uniform thickness in cross-section over the circumference of said profile.

* * * * *